US011832958B2

United States Patent
Jiang et al.

(10) Patent No.: US 11,832,958 B2
(45) Date of Patent: *Dec. 5, 2023

(54) AUTOMATIC IMAGE-BASED SKIN DIAGNOSTICS USING DEEP LEARNING

(71) Applicant: L'OREAL, Paris (FR)

(72) Inventors: Ruowei Jiang, Toronto (CA); Junwei Ma, Toronto (CA); He Ma, North York (CA); Eric Elmoznino, Toronto (CA); Irina Kezele, Toronto (CA); Alex Levinshtein, Thornhill (CA); Julien Despois, Paris (FR); Matthieu Perrot, Orsay (FR); Frederic Antoinin Raymond Serge Flament, Paris (FR); Parham Aarabi, Richmond Hill (CA)

(73) Assignee: L'OREAL, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 18/080,331

(22) Filed: Dec. 13, 2022

(65) Prior Publication Data

US 2023/0123037 A1    Apr. 20, 2023

Related U.S. Application Data

(63) Continuation of application No. 16/702,895, filed on Dec. 4, 2019, now Pat. No. 11,553,872.

(Continued)

(51) Int. Cl.
*A61B 5/00*    (2006.01)
*G06T 7/00*    (2017.01)
(Continued)

(52) U.S. Cl.
CPC .............. *A61B 5/441* (2013.01); *G06N 3/045* (2023.01); *G06N 3/08* (2013.01); *G06T 7/0012* (2013.01);
(Continued)

(58) Field of Classification Search
CPC ...... A61B 5/441; G06V 40/171; G06V 40/18; G06N 3/0454; G06N 3/08; G06T 7/0012; G06T 2207/30088
See application file for complete search history.

(56) References Cited

U.S. PATENT DOCUMENTS 6,128,608 A    10/2000   Barnhill et al.
6,157,921 A    12/2000   Barnhill et al.
(Continued)

FOREIGN PATENT DOCUMENTS

CN    103503029 A    1/2014
CN    108198620 A    6/2018
(Continued)

OTHER PUBLICATIONS

Shoieb, Doaa A., Sherin M. Youssef, and Walid M. Aly. "Computer-aided model for skin diagnosis using deep learning." Journal of Image and Graphics 4.2 (2016): 122-129.*

(Continued)

*Primary Examiner* — Shefali D Goradia
(74) *Attorney, Agent, or Firm* — Oblon, McClelland, Maier & Neustadt, L.L.P.

(57) ABSTRACT

There is shown and described a deep learning based system and method for skin diagnostics as well as testing metrics that show that such a deep learning based system outperforms human experts on the task of apparent skin diagnostics. Also shown and described is a system and method of monitoring a skin treatment regime using a deep learning based system and method for skin diagnostics.

20 Claims, 7 Drawing Sheets

Related U.S. Application Data

(60) Provisional application No. 62/775,117, filed on Dec. 4, 2018.

(51) Int. Cl.
  *G06V 40/16* (2022.01)
  *G06N 3/08* (2023.01)
  *G06V 10/82* (2022.01)
  *G06N 3/045* (2023.01)
  *G06V 10/44* (2022.01)
  *G06V 40/18* (2022.01)

(52) U.S. Cl.
  CPC ............ *G06V 10/454* (2022.01); *G06V 10/82* (2022.01); *G06V 40/171* (2022.01); *G06T 2207/30088* (2013.01); *G06V 40/174* (2022.01); *G06V 40/18* (2022.01)

(56) References Cited

U.S. PATENT DOCUMENTS

| | | |
|---|---|---|
| 6,427,141 B1 | 7/2002 | Barnhill et al. |
| 6,658,395 B1 | 12/2003 | Barnhill et al. |
| 6,714,925 B1 | 3/2004 | Barnhill et al. |
| 6,760,715 B1 | 7/2004 | Barnhill et al. |
| 6,789,069 B1 | 9/2004 | Barnhill et al. |
| 6,996,549 B2 | 2/2006 | Zhang et al. |
| 7,117,188 B2 | 10/2006 | Guyon et al. |
| 7,318,051 B2 | 1/2008 | Weston et al. |
| 7,353,215 B2 | 4/2008 | Bartlett et al. |
| 7,383,237 B2 | 6/2008 | Zhang et al. |
| 7,444,308 B2 | 10/2008 | Guyon et al. |
| 7,475,048 B2 | 1/2009 | Weston et al. |
| 7,542,947 B2 | 6/2009 | Guyon et al. |
| 7,542,959 B2 | 6/2009 | Barnhill et al. |
| 7,617,163 B2 | 11/2009 | Ben-Hur et al. |
| 7,624,074 B2 | 11/2009 | Weston et al. |
| 7,676,442 B2 | 3/2010 | Ben-Hur et al. |
| 7,788,193 B2 | 8/2010 | Bartlett et al. |
| 7,797,257 B2 | 9/2010 | Barnhill et al. |
| 7,805,388 B2 | 9/2010 | Weston et al. |
| 7,890,445 B2 | 2/2011 | Ben-Hur et al. |
| 7,921,068 B2 | 4/2011 | Guyon et al. |
| 7,970,718 B2 | 6/2011 | Guyon et al. |
| 8,008,012 B2 | 8/2011 | Guyon et al. |
| 8,095,483 B2 | 1/2012 | Weston et al. |
| 8,126,825 B2 | 2/2012 | Guyon et al. |
| 8,209,269 B2 | 6/2012 | Schoelkopf et al. |
| 8,275,723 B2 | 9/2012 | Barnhill et al. |
| 8,293,469 B2 | 10/2012 | Guyon et al. |
| 8,463,718 B2 | 6/2013 | Ben-Hur et al. |
| 8,489,531 B2 | 6/2013 | Ben-Hur et al. |
| 8,543,519 B2 | 9/2013 | Guyon et al. |
| 9,952,221 B2 | 4/2018 | Guyon et al. |
| 10,402,685 B2 | 9/2019 | Guyon et al. |
| 10,818,007 B2 | 10/2020 | Purwar et al. |
| 11,244,456 B2 | 2/2022 | Kaffenberger et al. |
| 2002/0165837 A1 | 11/2002 | Zhang et al. |
| 2003/0023571 A1 | 1/2003 | Barnhill et al. |
| 2003/0172043 A1 | 9/2003 | Guyon et al. |
| 2005/0071140 A1 | 3/2005 | Ben-Hur et al. |
| 2005/0071300 A1 | 3/2005 | Bartlett et al. |
| 2005/0131847 A1 | 6/2005 | Weston et al. |
| 2005/0165556 A1 | 7/2005 | Barnhill et al. |
| 2005/0216426 A1 | 9/2005 | Weston et al. |
| 2005/0228591 A1 | 10/2005 | Ben-Hur et al. |
| 2006/0064415 A1 | 3/2006 | Guyon et al. |
| 2006/0224539 A1 | 10/2006 | Zhang et al. |
| 2007/0092917 A1 | 4/2007 | Guyon et al. |
| 2008/0033899 A1 | 2/2008 | Barnhill et al. |
| 2008/0050836 A1 | 2/2008 | Guyon et al. |
| 2008/0059392 A1 | 3/2008 | Barnhill et al. |
| 2008/0097938 A1 | 4/2008 | Guyon et al. |
| 2008/0097939 A1 | 4/2008 | Guyon et al. |
| 2008/0097940 A1 | 4/2008 | Ben-Hur et al. |
| 2008/0140592 A1 | 6/2008 | Ben-Hur et al. |
| 2008/0215513 A1 | 9/2008 | Weston et al. |
| 2008/0233576 A1 | 9/2008 | Weston et al. |
| 2008/0301070 A1 | 12/2008 | Bartlett et al. |
| 2009/0215024 A1 | 8/2009 | Guyon et al. |
| 2009/0215058 A1 | 8/2009 | Guyon et al. |
| 2009/0226915 A1 | 9/2009 | Guyon et al. |
| 2009/0286240 A1 | 11/2009 | Guyon et al. |
| 2009/0305257 A1 | 12/2009 | Guyon et al. |
| 2010/0205124 A1 | 8/2010 | Ben-Hur et al. |
| 2010/0256988 A1 | 10/2010 | Barnhill et al. |
| 2010/0318482 A1 | 12/2010 | Bartlett et al. |
| 2011/0078099 A1 | 3/2011 | Weston et al. |
| 2011/0106735 A1 | 5/2011 | Weston et al. |
| 2011/0119213 A1 | 5/2011 | Elisseeff et al. |
| 2011/0125683 A1 | 5/2011 | Ben Hur et al. |
| 2011/0184896 A1 | 7/2011 | Guyon et al. |
| 2011/0312509 A1 | 12/2011 | Guyon et al. |
| 2012/0008838 A1 | 1/2012 | Guyon et al. |
| 2013/0297607 A1 | 11/2013 | Ben-Hur et al. |
| 2014/0018249 A1 | 1/2014 | Guyon et al. |
| 2014/0032451 A1 | 1/2014 | Ben-Hur et al. |
| 2015/0339448 A1 | 11/2015 | Guyon et al. |
| 2017/0246473 A1 | 8/2017 | Marinkovich et al. |
| 2018/0130203 A1 | 5/2018 | Abedini et al. |
| 2018/0289334 A1 | 10/2018 | De Brouwer et al. |
| 2018/0321245 A1 | 11/2018 | Guyon et al. |
| 2018/0350071 A1 | 12/2018 | Purwar et al. |
| 2019/0223728 A1 | 7/2019 | Heidari et al. |

FOREIGN PATENT DOCUMENTS

| | | |
|---|---|---|
| JP | 2016-148906 A | 8/2016 |
| WO | WO 2011/087807 A2 | 7/2011 |
| WO | WO 2017/165363 A1 | 9/2017 |
| WO | WO 2018/146688 A1 | 8/2018 |
| WO | WO 2020/113326 A1 | 6/2020 |

OTHER PUBLICATIONS

Li, Yuexiang, and Linlin Shen. "Skin lesion analysis towards melanoma detection using deep learning network." Sensors 18.2 (2018): 556.*

Hu, Zilong, et al. "Deep learning for image-based cancer detection and diagnosis—A survey." Pattern Recognition 83 (2018): 134-149.*

International Search Report and Written Opinion dated Feb. 26, 2020 in PCT/CA2019/051735, 11 pages.

C. Chen et al., "Facial Skin Image Classification System Using Convolutional Neural Networks Deep Learning Algorithm," 2018 9th International Conference on Awareness Science and Technology (iCAST), Fukuoka, Sep. 2018, pp. 51-55.

Patnaik S. K et al., "Automated Skin Disease Identification using Deep Learning Algorithm", Biomed Pharmacology Journal, India, vol. 11(3), Sep 2018, pp. 1429-1436.

Extended European Search Report dated Jul. 11, 2022 in European Patent Application No. 19892814.5, 8 pages.

Yan, Z., et al., "HD-CNN: Hierarchical Deep Convolutional Neural Networks for Large Scale Visual Recognition", 2015 IEEE International Conference on Computer Vision (ICCV), IEEE, Dec. 7, 2015, XP032866619, pp. 2740-2748.

Demyanov, S., et al., "Tree-Loss function for training neural networks on weakly-labelled datasets", 2017 IEEE 14th International Symposium on Biomedical Imaging (ISBI) IEEE Piscataway, NJ, USA, Apr. 1, 2017, XP055936938, pp. 287-291.

Harangi, B., Ed., "Skin lesion classification with ensembles of deep convolutional neural networks", Journal of Biomedical Informatics, Academic Press, vol. 86, Aug. 10, 2018, XP085497086, pp. 25-32.

Chinese Office Action dated Jul. 22, 2023, issued in Chinese Patent Application No. 201980091094.9.

Chiun-Li Chin et al. "Facial skin image classification system using Convolutional Neural Networks deep learning algorithm." Sep. 19, 2018, XP033433896.

Japanese Office Action dated Jul. 7, 2023, issued in Japanese Patent Application No. 2021-554782 (with English translation).

(56) References Cited

OTHER PUBLICATIONS

Xulei Yang et al. "Skin Lesion Analysis by Multi-Target Deep Neural Networks." [online], 2018 https://ieeexplore.ieee.org/document/8512488.

* cited by examiner

AUTOMATIC IMAGE-BASED SKIN DIAGNOSTICS USING DEEP LEARNING

CROSS-REFERENCE

This application is a continuation of U.S. patent application Ser. No. 16/702,895, filed on Dec. 4, 2019, which claims, in respect of the United States, a domestic benefit of, and in respect of all other jurisdiction, a Paris Convention priority to U.S. Provisional Patent Application No. 62/775,117 filed Dec. 4, 2018, the contents of which are incorporated herein by reference where permissible.

FIELD

The present document relates to skin diagnostics such as for dermatology and to skin treatment monitoring and more particularly to a system and method for automatic image-based skin diagnostics using deep learning.

BACKGROUND

Accurate skin analysis is an important area in both medical and cosmetics domains. Images of skin may be generated and analysed to determine one or more skin conditions. It is desirable to solve the skin analysis problem purely from observing skin through images—an apparent skin diagnostics task—using computer technology. A successful solution of this problem would make skin analysis faster and cheaper, as it would no longer require people to be examined in person by dermatologists.

Images such as images of a face present one or more skin conditions in an encoded manner within pixels of the images. It is desired to provide a computer implemented method, a computing device, and other aspects that perform or enable performance of automatic image-based skin diagnostics using deep learning to decode the one or more skin conditions from the images.

SUMMARY

There is shown and described a deep learning based system and method for skin diagnostics as well as testing metrics that show that such a deep learning based system outperforms human experts on the task of apparent skin diagnostics. Also shown and described is a system and method of monitoring a skin treatment regime using a deep learning based system and method for skin diagnostics.

There is provided a skin diagnostic device comprising: a storage unit to store and provide a convolutional neural network (CNN) configured to classify pixels of an image to determine a plurality (N) of respective skin sign diagnoses for each of a plurality (N) of respective skin signs wherein the CNN comprises a deep neural network for image classification configured to generate the N respective skin sign diagnoses and wherein the CNN is trained using skin sign data for each of the N respective skin signs; and a processing unit coupled to the storage unit configured to receive the image and process the image using the CNN to generate the N respective skin sign diagnoses.

The CNN may comprise: an encoder phase defined from a pre-trained network for image classification and configured to encode features to a final encoder phase feature net; and a decoder phase configured to receive the final encoder phase feature net for decoding by a plurality (N) of respective parallel skin sign branches to generate each of the N respective skin sign diagnoses. The decoder phase includes a global pooling operation to process the final encoder phase feature net to provide to each of the N respective parallel skin sign branches. The CNN may be further configured to classify the pixels to determine an ethnicity vector and the CNN is trained using skin sign data for each of the N respective skin signs and a plurality of ethnicities. The decoder phase may comprise a further parallel branch for ethnicity to generate the ethnicity vector.

Each branch of the N respective parallel skin sign branches may comprise in succession: a first fully connected layer followed, a first activation layer, a second fully connected layer, a second activation layer and a final activation layer to output a final value comprising one of the N respective skin sign diagnoses and the ethnicity vector. The final activation layer may be defined in accordance with a function of equation (1) for an input score x received from the second activation layer:

$$LeakyClamp(x) = \begin{cases} x & \text{if } x \in [a, b] \\ \alpha(x-a) + a & \text{if } x < a \\ \alpha(x-b) + b & \text{if } x > b \end{cases} \quad (1)$$

where $\alpha$ is a slope, a is a lower bound and b is an upper bound of a respective score range for each the N respective skin sign diagnoses.

The CNN may be one trained using multiple samples in the form $(x_i, y_i)$, with $x_i$ being the i-th training image and $y_i$ being a corresponding vector of ground truth skin sign diagnoses; and trained to minimize a loss function for each respective branch of the N parallel skin sign branches and the further parallel branch for ethnicity. The CNN may be one further trained to minimize a loss function L, comprising a L2 loss function for each of the N respective skin sign branches in a weighted combination with a standard cross-entropy classification loss $L_{ethnicity}$ for the further parallel branch for ethnicity, according to equation (3):

$$L = L2 + \lambda L_{ethnicity} \quad (3)$$

where $\lambda$ controls a balance between a score regression and ethnicity classification losses.

The storage unit may store a face and landmark detector to pre-process the image and the processing unit may be configured to generate a normalized image from the image using the face and landmark detector and use the normalized image when using the CNN.

The CNN may initially comprise a pre-trained network for image classification which is adapted to generate the N respective skin sign diagnoses by: removing the fully connected layers of the pre-trained network; and defining N respective groups of layers to decode a same feature net for each of the N respective skin sign diagnoses in parallel.

The skin diagnostic device may be configured as one of: a computing device for personal use comprising a mobile device; and a server providing skin diagnostic services via a communications network.

The storage unit may store code which when executed by the processing unit provides a treatment product selector responsive to at least some of the N skin sign diagnoses to obtain a recommendation for at least one of a product and a treatment plan.

The storage unit may store code which when executed by the processing unit provides an image acquisition function to receive the image.

The storage unit may store code which when executed by the processing unit provides a treatment monitor to monitor treatment for at least one skin sign.

The processing unit may be configured to at least one of remind, instruct and/or record treatment activities associated with a product application for respective treatment sessions.

The processing unit may be configured to process a second image using the CNN to generate a subsequent skin diagnoses received following a treatment session. The storage unit may store code which when executed by the processing unit provides a presentation of comparative results using the subsequent skin diagnoses.

There is provided a computer implemented method of skin diagnoses comprising: providing a storage unit to store and provide a convolutional neural network (CNN) configured to classify pixels of an image to determine a plurality (N) of respective skin sign diagnoses for each of a plurality (N) of respective skin signs wherein the CNN comprises a deep neural network for image classification configured to generate the N respective skin sign diagnoses and wherein the CNN is trained using skin sign data for each of the N respective skin signs; and performing by a processing unit coupled to the storage unit: receiving the image; and processing the image using the CNN to generate the N respective skin sign diagnoses.

There is a second method comprising: training a convolutional neural network (CNN) configured to classify pixels of an image to determine a plurality (N) of respective skin sign diagnoses for each of a plurality (N) of respective skin signs wherein the CNN comprises a deep neural network for image classification configured to generate the N respective skin sign diagnoses and wherein the training is performed using skin sign data for each of the N respective skin signs.

These and other aspects will be apparent to a person of ordinary skill in the art including computer program product aspects where a (non-transient) storage unit stores instructions, which when executed by a processing unit, configure operations of a computing device to perform any of the computer-implemented method aspects herein.

Figure 1:
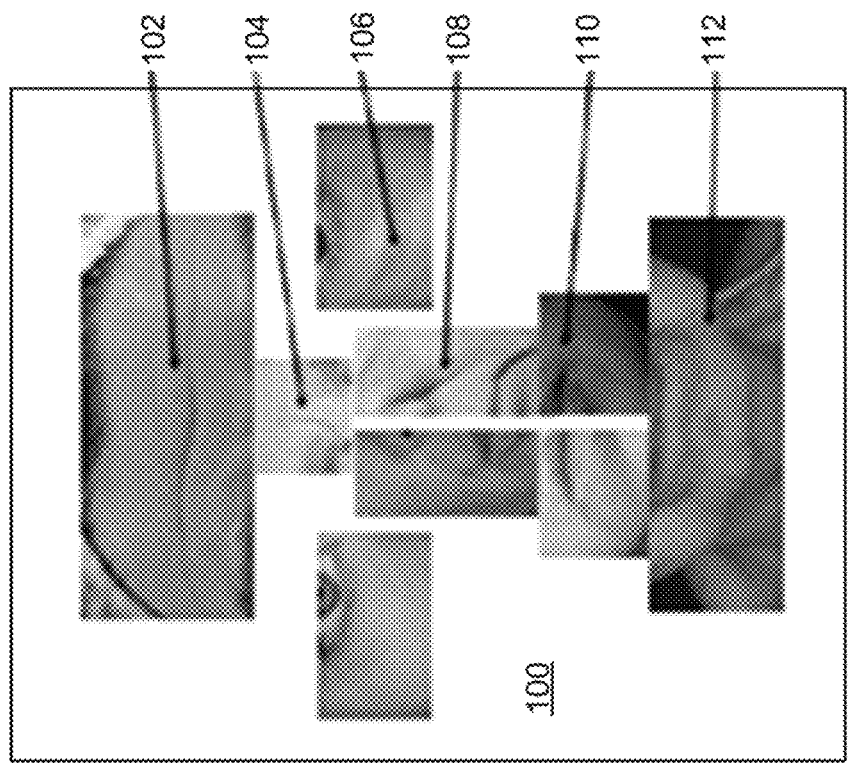
FIG. 1 is a photo composite showing skin signs.

The present inventive concept is best described through certain embodiments thereof, which are described herein with reference to the accompanying drawings, wherein like reference numerals refer to like features throughout. It is to be understood that the term invention, when used herein, is intended to connote the inventive concept underlying the embodiments described below and not merely the embodiments themselves. It is to be understood further that the general inventive concept is not limited to the illustrative embodiments described below and the following descriptions should be read in such light.

DETAILED DESCRIPTION

Introduction

The term "skin sign" or "sign" herein references a particular skin condition such as (but not limited to), nasolabial folds, variously located wrinkles; ptosis of the lower part of the face; sebaceous pores; whole face pigmentation; and vascular disorders. FIG. 1 is a photo composite 100 showing skin signs such as forehead wrinkles 102, glabellar wrinkles 104, underneath the eye wrinkles 106, nasolabial fold 108, wrinkles of the corner of the lip 110 and ptosis of the lower part of the face 112. The appearance of the human face undergoes structural changes that are induced by a variety of factors. These comprise chronological aging, photo-aging, food-related habits (anorexia or obesity), lifestyle factors (sleeping issues, smoking, alcoholism, etc.). These structural changes obviously most concern localized wrinkles (e.g., forehead, glabellar, upper-lip), but are often accompanied by a global sagging (ptosis) of the facial appearance (e.g., drooping eyelids, eye-sagging, ptosis of the neck) or presence of enlarged skin pores on the cheeks. All these changes, which may subtly progress through years and decades, are differently expressed according to gender and ethnicity. And they are accentuated by variable exposure(s) to sun (UV's) in addition to their well-known impacts (associated or not with aerial pollution) upon the skin pigmentation (lentigines, dark spots, skin darkening) or upon the vascular cutaneous network (redness, telangiectasia, etc.)

Grading the various severities of some facial signs is an important need for different purposes, being dermatological (skin peelings, corrective surgery, etc.), cosmetic (skin care, anti-aging products) or as a possible help/advice to consumers. Such a need does not only respond to a chief scientific objectivity—it may also serve the detection of false product claims. This grading objective was reached by the availability of a multi-volume referential skin atlas from L'Oreal S.A (R. Bazin, E. Doublet, in: P. E. Med'Com (Ed.), Skin Aging Atlas. Volume 1, Caucasian Type, 2007. R. Bazin, F. Flament, in: P. E. Med'Com (Ed.), Skin Aging Atlas. Volume 2, Asian Type, 2010. R. Bazin, F. Flament, F. Giron, in: P. E. Med'Com (Ed.), Skin Aging Atlas. Volume 3, Afro-American Type, 2012. R. Bazin, F. Flament, V. Rubert, in: P. E. Med'Com (Ed.), Skin Aging Atlas. Volume 4, Indian Type, 2015. And, F. Flament, R. Bazin, H. Qiu, in: P. E. Med'Com (Ed.), Skin Aging Atlas. Volume 5, Photo-aging Face & Body, 2017). This skin atlas standardized the visual gradings (and their respective scales of increased severities, i.e. 0 to 4, 5, 6 or 7) of more than 20 facial signs, in both genders of four ethnicities with age, through professionally processed photographs. Zooming on a given sign, irrespective of the global facial appearance, allowed skin experts to attribute, in blind, a grade to a facial sign within its respective scale of severity. These skin atlases showed that the aging process differently affects people in accordance with gender, but within a same gender the effects are similar. However, some changes in facial signs were ethnicity specific. Apart from affording a precise description of the changes of facial signs with aging, in both genders of four ethnicities, this approach led to a determination that some facial signs are more concerned with or related to fatigue induced by a single day of work, in Caucasian or Chinese women. Yet, another challenging and important step remained to be explored: could there be developed an automatic process, free from human assessments, that could grade some structural facial signs through either standardized photographs or those taken by mobile phones (e.g. through "selfies" and selfie videos) under variable real-life conditions of lightning and during human activities (work, sport, riding in transportation, etc.) In short, obtaining quantified data from a "blind/neutral" automatic system is desired by many possible applications.

Thus there is described a deep learning approach to skin diagnostics developed using data of females of different ages and ethnicities including the technical aspects of this approach and the results obtained. A comparisons with data obtained by expert grading (using skin atlases) is also presented.

Figure 2:
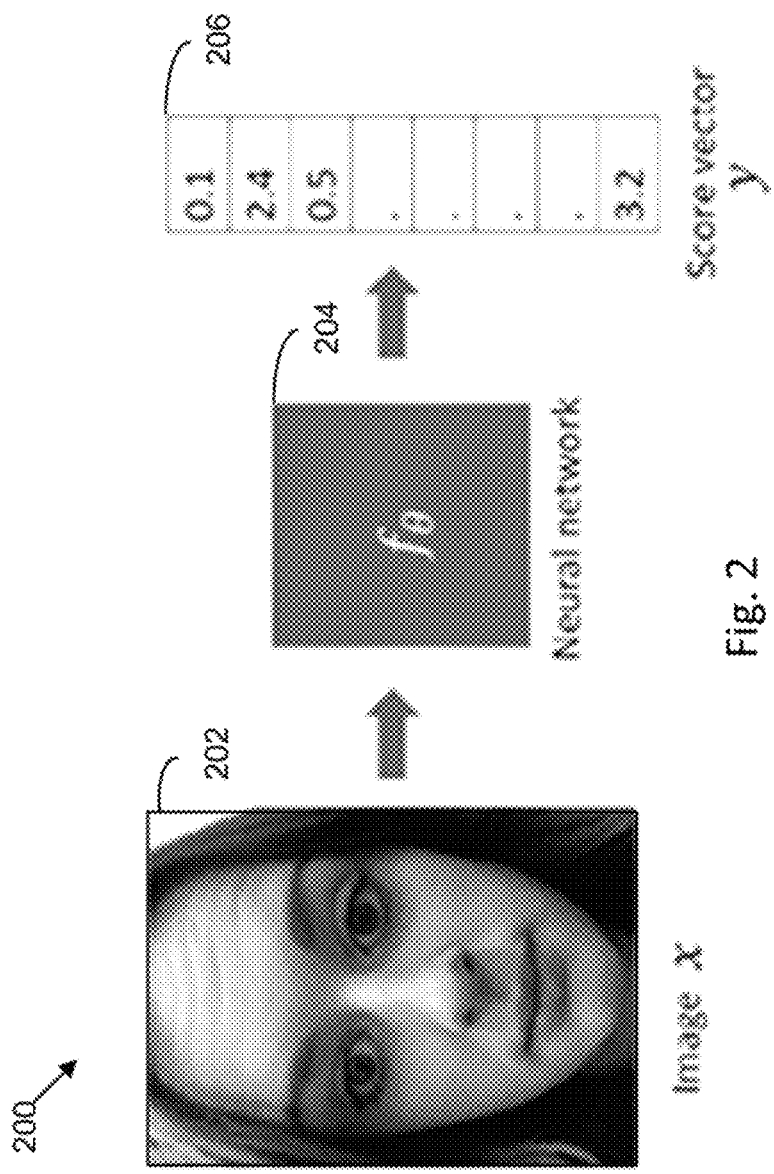
FIG. 2 is a schematic illustration of a deep learning system in accordance with an embodiment or example herein.

The apparent skin diagnostics problem, whereby skin signs are assessed from only an image, is cast as a supervised regression problem for computer implementation using deep learning. As represented by the schematic illustration of FIG. 2 showing a deep learning system 200, at test or live run time, given a facial image x 202, a neural network 204 of system 200 returns a vector of scores y 206 where $y=f_\theta(x)$, and where $f_\theta$ is the neural network 204 parameterized by $\theta$. Each component of y 206 corresponds to a different skin sign. Other skin ratings or factors such as ethnicity may also be determined as described further.

While it is possible to design separate neural networks for each skin sign, the similarity in learned low-level features across signs allows an implementation of the above approach where all the signs are estimated jointly by a single network. A side benefit is a higher computational efficiency.

Rather than designing a neural network from scratch, architectures proven to work well on a variety of tasks may be adapted. In particular, the ResNet50 (a 50 layer Residual Network from Microsoft Research Asia as described by K. He, X. Zhang, S. Ren, J. Sun, Deep Residual Learning for Image Recognition, in: Proceedings of the IEEE conference on computer vision and pattern recognition, 2016, pp. 770-778, incorporated herein in its entirety) and the MobileNet V2 (the second version of the depthwise separable convolutional neural network from Google Inc. as described by M. Sandler, A. Howard, M. Zhu, A. Zhmoginov, L.-C. Chen, Inverted Residuals and Linear Bottlenecks: Mobile Networks for Classification, Detection and Segmentation, arXiv preprint arXiv: 1801.04381, 13 Jan. 2018 incorporated herein in its entirety) architectures may be adapted.

ResNet50 and MobileNetV2 are convolutional neural networks trained on ImageNet (an open source database of image data for classification). ResNet50 is used as the backbone of many state-of-the-art systems, and MobileNetV2 is a more efficient network that can be used if running time and storage space are a concern, at a reasonable degradation in accuracy. When used for classification, each of these networks contains a large fully convolutional part resulting in a low resolution but powerful set of CNN features (e.g. in an encoder phase), followed by global max or average pooling and several fully connected layers with a final classification layer (in a decoder phase). Each makes a good candidate for adaptation.

Figure 3:
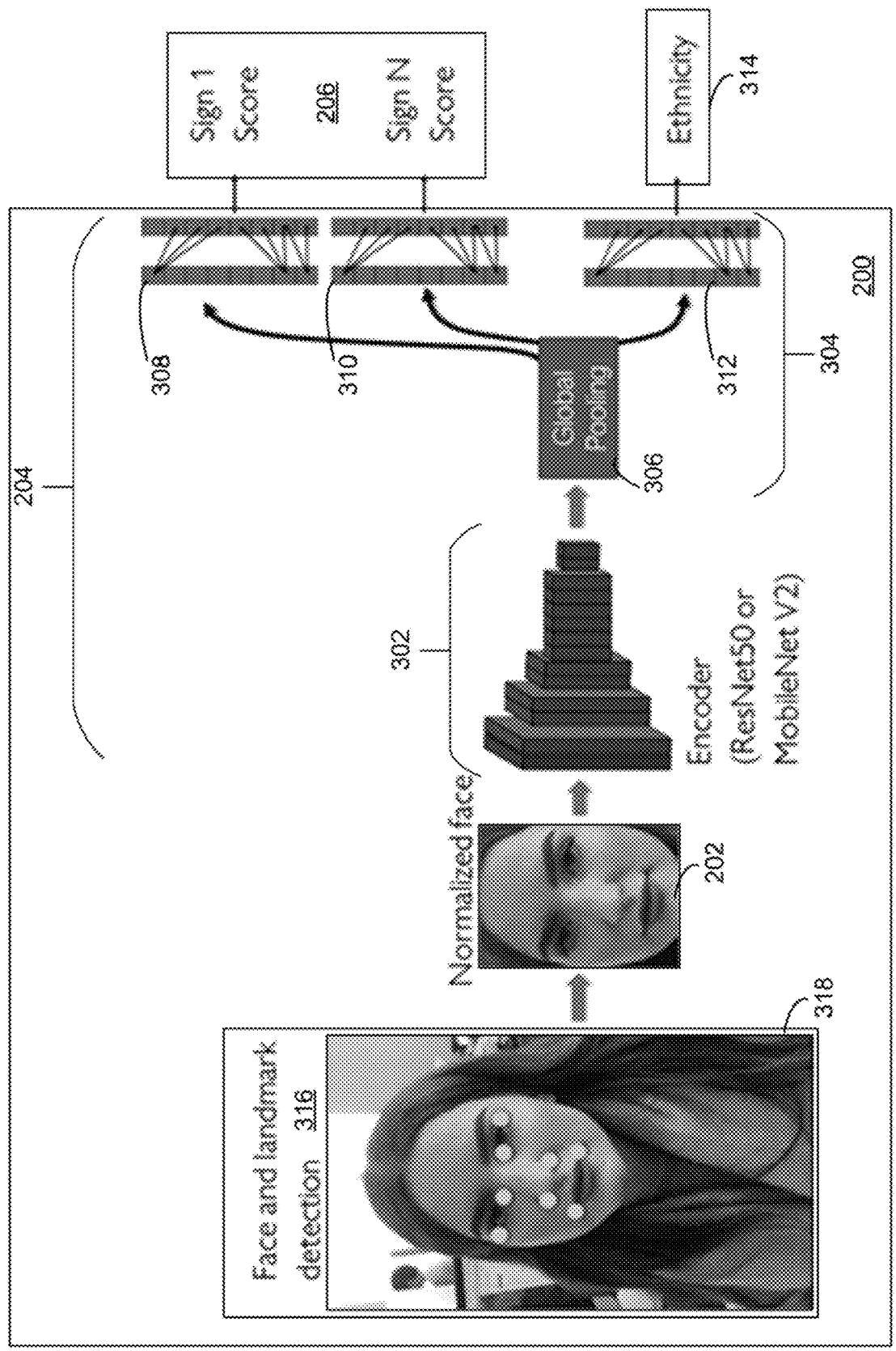
FIG. 3 is a schematic illustration of the deep learning system of FIG. 2 in more detail.

FIG. 3 is a schematic illustration of the deep learning system 200 in more detail showing neural network 202 comprising encoder components 302 defined by layers (e.g. components with respective operations) from a source network such as ResNEt50 or MobileNetV2 as well as decoder components 304. Decoder components 304 comprise a global max pooling layer 306 and respective parallel branches (e.g. 308, 310, and 312 shown for simplification, it being understood that for N skin signs there are N+1 parallel branches) for decoding each of the N skin signs in output vector 206 and an ethnicity factor (output 314).

Rather than replacing just the final classification layer, each of the source networks is cropped after the pooling layer to construct the feature net (neural network 204). Specifically, ResNet50 is cropped after its average pooling layer and the average pooling layer is replaced with global max pooling layer (e.g. 306), yielding a 1×1×2048 feature vector. Similarly for MobileNetV2 the fully connected layers are cropped and the average pooling layer is replaced by a global max pooling layer such that the new feature net outputs a 1×1×1280 feature vector. Each of the parallel branches 308, 310, and 312 receives the output from global max pooling layer 306.

This early branching choice was made due to a dependence of different skin signs on potentially different image features and the choice is verified through experiments. Each skin sign branch (one of the respective parallel branches 308, 310) comprises of two fully connected layers each followed by an activation layer. It first connects the feature net (ResNet50 or MobileNet) by a fully connected layer with input size as the feature size after pooling (e.g. 1×1×2048 or 1×1×1280, respectively) and output size 50, followed by a ReLU activation layer (e.g. a rectified linear activation unit). The second fully connected layer with input size 50 and output size 1, is then followed by a customized activation layer which outputs the final score.

The system conforms to the internationally accepted skin score atlas maintained by L'Oreal as referenced above herein, and as a result skin signs have individual scales depending on their type, person's ethnicity, and gender. Since each skin sign has a bound. Rather than having a purely linear regression layer or other activation function for the last layer, a custom function is used, namely, a Leaky ReLU-like activation function (named LeakyClamp). Leaky ReLU is described in A. L. Maas, A. Y. Hannun, A. Y. Ng, Rectifier Nonlinearities Improve Neural Network Acoustic Models, in: Proc. International Conference on Machine Learning, Vol. 30, 2013, p. 3, incorporated herein by reference. Leaky ReLUs seek to address a "dying ReLU" problem when x<0. Instead of the standard ReLU function being zero when x<0, a leaky ReLU has a small negative slope (e.g. close to zero, of 0.01, or so).

LeakyClamp has a slope close to zero below min-activation and above max-activation, where max-activation is different depending on the sign as per equation 1:

$$LeakyClamp(x) = \begin{cases} x & \text{if } x \in [a, b] \\ \alpha(x-a)+a & \text{if } x < a \\ \alpha(x-b)+b & \text{if } x > b \end{cases} \quad (1)$$

where $\alpha$ is the slope, a is the lower bound and b is the upper bound of score range. In training, choose $\alpha$ is chosen to be 0.01 and a, b to be the score range for each sign.

To train the deep learning network, multiple samples in the form $(x_i, y_i)$, with $x_i$ being the i-th training image and $y_i$ being the corresponding vector of scores are obtained and used as described further herein in the evaluation section. To find the best set of parameters $\theta$ a loss function is minimized. Experiments were performed with several loss functions, but no advantage was found of one over the other.

Therefore, the standard L2 loss (eq. 2) was minimized and is used in the data shown herein where L2 is:

$$\arg\min_\theta \sum_i \|y_i - f_\theta(x_i)\|^2 \qquad (2)$$

Moreover, due to the dependence of skin scores on ethnicity, there is defined a separate ethnicity prediction branch (one of the respective parallel branches 312) with its own component structure and an additional standard cross-entropy classification loss $L_{ethnicity}$. The ethnicity branch (312) has one fully connected layer with input size as the feature size and output size as the number of ethnicities. The extra loss $L_{ethnicity}$ helps guide the training in the right direction, but is also assistive at test time so that the output score can be interpreted correctly by using the person's ethnicity group. The L2 loss and cross-entropy classification loss $L_{ethnicity}$ are combined with a weight λ into a loss L as set out in equations 3:

$$L = \Sigma_i \|y_i - f_\theta(x_i)\|^2 + \lambda L_{ethnicity} \qquad (3)$$

with λ controlling the balance between the score regression and the ethnicity classification losses. In training, λ=0.002 was used.

Following a common transfer learning practice, the network is pre-trained on ImageNet and then fine-tuned on the skin diagnostics data using (e.g. minimizing) the above loss. There is also applied the same image normalization as the pre-training procedure for ImageNet, centered at [0.485, 0.456, 0.406] with a standard deviation of [0.229, 0.224, 0.225]. An Adam optimizer, first-order gradient-based optimization of stochastic objective functions is used, with learning rate 0.0001 and batch size 16 in fine-tuning training process. Adam is described in D. P. Kingma, J. Ba, Adam: A method for stochastic optimization, CoRR abs/1412.6980. arXiv: 1412.6980 as early as 22 Dec. 2014 and is incorporated herein by reference.

There are numerous scientific, commercial and other applications for apparent skin diagnostics, including consumer applications. While it may be possible to control the imaging conditions for some such applications by taking images in controlled lighting conditions and utilizing a standardized pose, such may not be feasible, especially in a consumer application. Thus a deep learning system may be desired to be able to handle a variety of lighting conditions and facial poses. With reference still to FIG. 3, to deal with the latter, images may be pre-processed to be normalized using, in one example, a facial landmark detector 316, (such as is described in V. Kazemi, J. Sullivan, One millisecond face alignment with an ensemble of regression trees, in: IEEE Conference on Computer Vision and Pattern Recognition, 2014, pp. 1867-1874, incorporated herein by reference) on a source input image 318 to normalize the face (outputting image 202) based on detected landmarks. In this way, an input facial image x is always an upright frontal image of a face at a fixed scale.

During training, training data may be augmented with crops of a different scales (randomly chosen from 0.8 to 1.0) to handle any scale variation even after the landmark-based cropping. After randomly cropping the image, each input image is resized to a resolution of 448 pixels by 334 pixels (e.g. to match the expected input resolution of the source networks). In addition, selected images are randomly flipped horizontally with a probability of 0.5 during the training process. To deal with the lighting variation, training is performed with images having a variety of lighting conditions, as mentioned in the evaluation section herein.

Evaluation

The model is trained results evaluated on two datasets of female images according to the following nine skin signs:
Nasolabial folds;
Glabellar wrinkles;
Forehead wrinkles;
Underneath the eye wrinkles;
Corner of the lips wrinkles;
Ptosis of the lower part of the face;
Cheek sebaceous pores;
Whole face pigmentation; and
Vascular disorders.

Note that the last two skin signs are defined only for Caucasian and Asian ethnicities. The first dataset consists of 5834 female images taken using a professional camera in controlled laboratory conditions with an ideal lighting and face pose (subsequently called the "clinical dataset"). Note that not all the images in this dataset contain ground truth for all the nine signs. The second dataset consists of selfie images taken by mobile phones in uncontrolled lighting conditions (subsequently called the "selfie dataset"). It contains 380 female images of three ethnicities (Caucasian, Asian, and African), with each person captured in four different lighting conditions: outdoor daylight, indoor daylight, indoor artificial diffuse light, and indoor artificial direct light. This results in a total of 4560 images. For both datasets, 90% of the data was used for training and 10% for testing. Likewise, in both cases the same face normalization framework is applied, despite it not being necessary for some of the images in the clinical dataset. This framework fails to detect the face and the facial landmarks in some of the images, and as such, the amount of training and test data is slightly reduced.

Both datasets were annotated manually by expert dermatologists, with each image being annotated by ten to twelve experts. The average expert prediction is taken as the ground truth.

Training on and for male images may be undertaken. Imaging conditions may be imposed such as in relation to no facial hair to obtain clear images. Facial hair would not only greatly affect the scores for signs in skin regions covered with facial hair, but this would also affect the training overall as the features are trained for all signs together. The skin signs for males and females are the same.

Several measures are used to evaluate the trained deep learning system 200 comprising neural network 202. For ethnicity prediction, the percentage being correctly classified is measured. Test accuracy for clinical dataset and selfies dataset are 99.7% and 98.2% correspondingly. For skin scores, two kinds of measurement are used. The first is the mean absolute error (M AE), which is the average of the absolute differences between the predicted and the ground truth scores across all the samples. However, a more meaningful error measure is the fraction of samples for which the absolute error is below some threshold (% (M AE<T)). Depending on the application, this threshold can be more or less strict; thus, this error measure is reported for several different thresholds. Below are the results for both clinical and selfie datasets.

Table 1 shows the results on the clinical dataset and Table 2 shows the results on the selfie dataset. Observe, for example, that while the typical range of scores is from 0 to 5-10, the deep learning system 200 is able to predict the score within an absolute error of 1 in over 90% for any skin sign (and much more accurately for some signs).

TABLE 1

Automatic skin diagnostics accuracy on the clinical dataset

| | Nasolabial fold | Glabellar wrinkles | Forehead wrinkles | Underneath the eye wrinkles | Corner of the lips wrinkles | Ptosis of the lower part of the face | Cheek sebaceous pores | Whole-face pigmentation | Vascular disorders |
|---|---|---|---|---|---|---|---|---|---|
| MAE | 0.3313 | 0.2935 | 0.348 | 0.4346 | 0.3647 | 0.2962 | 0.3466 | 0.4546 | 0.3727 |
| %(MAE < 0.5) | 78 | 84 | 77 | 67 | 76 | 80 | 77 | 68 | 82 |
| %(MAE < 1.0) | 94 | 97 | 96 | 93 | 94 | 99 | 95 | 91 | 93 |
| %(MAE < 1.5) | 100 | 99 | 99 | 98 | 98 | 100 | 100 | 95 | 96 |

TABLE 2

Automatic skin diagnostics accuracy on the selfies dataset

| | Nasolabial fold | Glabellar wrinkles | Forehead wrinkles | Underneath the eye wrinkles | Corner of the lips wrinkles | Ptosis of the lower part of the face | Cheek sebaceous pores | Whole-face pigmentation | Vascular disorders |
|---|---|---|---|---|---|---|---|---|---|
| MAE | 0.3581 | 0.2599 | 0.3528 | 0.325 | 0.3287 | 0.2962 | 0.3316 | 0.7628 | 0.2311 |
| %(MAE < 0.5) | 74 | 85 | 76 | 80 | 79 | 82 | 79 | 53 | 91 |
| %(MAE < 1.0) | 96 | 99 | 96 | 98 | 97 | 98 | 98 | 73 | 100 |
| %(MAE < 1.5) | 100 | 100 | 100 | 100 | 100 | 100 | 100 | 85 | 100 |

For the selfies dataset (Table 2) the results are even better in most cases, despite less controlled lighting conditions. However, it is also observed that experts themselves have a very large variation in scores among themselves and even across different lighting conditions for the same expert. The ground truth is therefore biased and it is likely that system 200 internally learns to predict the lighting condition to better predict the score. It may be assistive to collect a more consistent ground truth across different lighting conditions.

Currently, however, the data shows that scoring skin signs based on "in-the-wild" images is a difficult task even for expert dermatologists, and system 200 outperforms them in this task. This is seen in Table 3, the absolute error for each image is calculated by comparing each expert's prediction to the average experts' prediction for this image, as each image was scored by 12 experts, on average. By comparing Tables 2 and 3, it can be observed that system 100 is more accurate than experts for every sign, with exception of Whole face pigmentation.

In addition to model validation on image-based scores for selfies data, validation is also performed on a subset of the test subjects for which the dermatologists were able to score the skin condition signs in person. Expert dermatologists received visits from 68 subjects (around 12 experts per subject), and assessed them live, without regard to the subject image-based scores. Similarly to image-based analysis, the mean absolute error was calculated for each skin condition sign, for: 1) the model in system 200, by comparing the prediction from the model to the average experts' score for the sign for the particular test subject, and 2) for expert in person assessment, by comparing each expert's score vector to the average experts' score vector for this subject. The two tables related to: model performance (Table 4), and to expert performance (Table 5) are shown below. Even in this case of in-person expert scoring, similar to the case of image-based scoring, automatic score prediction from system 200 results in a higher accuracy than the prediction by expert dermatologists, and here, for all the signs.

TABLE 3

Experts accuracy on the selfies dataset

| | Nasolabial fold | Glabellar wrinkles | Forehead wrinkles | Underneath the eye wrinkles | Corner of the lips wrinkles | Ptosis of the lower part of the face | Cheek sebaceous pores | Whole-face pigmentation | Vascular disorders |
|---|---|---|---|---|---|---|---|---|---|
| MAE | 0.5705 | 0.4799 | 0.475 | 0.6925 | 0.6589 | 0.5558 | NaN | 0.7594 | 0.4779 |
| M(AE < 0.5) | 0.5336 | 0.6421 | 0.62 | 0.4355 | 0.4759 | 0.5451 | NaN | 0.459 | 0.6461 |
| M(AE < 1.0) | 0.8357 | 0.8834 | 0.899 | 0.7608 | 0.7898 | 0.8482 | NaN | 0.7347 | 0.8777 |
| M(AE < 1.5) | 0.9542 | 0.9618 | 0.976 | 0.9182 | 0.9217 | 0.9593 | NaN | 0.8651 | 0.9586 |

TABLE 4

Automatic skin diagnostics accuracy on 'in-person' validation dataset

|  | Nasolabial fold | Glabellar wrinkles | Forehead wrinkles | Underneath the eye wrinkles | Corner of the lips wrinkles | Ptosis of the lower part of the face | Cheek sebaceous pores | Whole-face pigmentation | Vascular disorders |
|---|---|---|---|---|---|---|---|---|---|
| MAE | 0.4875 | 0.6801 | 0.6905 | 0.5834 | 0.5771 | 0.4201 | 0.5735 | 0.5206 | 0.6193 |
| %(MAE < 0.5) | 60 | 46 | 44 | 52 | 46 | 69 | 53 | 57 | 50 |
| %(MAE < 1.0) | 88 | 76 | 79 | 84 | 86 | 93 | 82 | 88 | 78 |
| %(MAE < 1.5) | 97 | 92 | 91 | 96 | 97 | 100 | 93 | 97 | 94 |

TABLE 5

Experts accuracy on 'in-person' validation dataset

|  | Nasolabial fold | Glabellar wrinkles | Forehead wrinkles | Underneath the eye wrinkles | Corner of the lips wrinkles | Ptosis of the lower part of the face | Cheek sebaceous pores | Whole-face pigmentation | Vascular disorders |
|---|---|---|---|---|---|---|---|---|---|
| MAE | 0.818 | 0.78303 | 0.75794 | 0.84688 | 0.85783 | 0.73194 | 0.83505 | 0.8176 | 0.93112 |
| %(MAE < 0.5) | 38 | 43 | 44 | 42 | 39 | 44 | 35 | 39 | 38 |
| %(MAE < 1.0) | 67 | 68 | 72 | 67 | 67 | 73 | 66 | 70 | 65 |
| %(MAE < 1.5) | 86 | 86 | 89 | 83 | 83 | 89 | 86 | 85 | 80 |

For better understanding of the results in Tables 4, and 5, the same validation analysis is performed as in Tables 2, and 3, but using only the subset of 68 subjects that were assessed in person. The results are shown below in Tables 6, and 7. Again, a significantly higher accuracy is obtained with the model score prediction from system 200 than by expert scoring.

TABLE 6

Automatic skin diagnostics accuracy on a subset of 68 subjects

|  | Nasolabial fold | Glabellar wrinkles | Forehead wrinkles | Underneath the eye wrinkles | Corner of the lips wrinkles | Ptosis of the lower part of the face | Cheek sebaceous pores | Whole-face pigmentation | Vascular disorders |
|---|---|---|---|---|---|---|---|---|---|
| MAE | 0.3529 | 0.2509 | 0.3176 | 0.3512 | 0.364 | 0.3162 | 0.2927 | 0.335 | 0.2572 |
| %(MAE < 0.5) | 76 | 89 | 80 | 74 | 76 | 79 | 83 | 75 | 85 |
| %(MAE < 1.0) | 96 | 100 | 98 | 97 | 96 | 97 | 97 | 97 | 98 |
| %(MAE < 1.5) | 100 | 100 | 99 | 99 | 98 | 100 | 100 | 100 | 100 |

TABLE 7

Experts accuracy on a subset of 68 subjects

|  | Nasolabial fold | Glabellar wrinkles | Forehead wrinkles | Underneath the eye wrinkles | Corner of the lips wrinkles | Ptosis of the lower part of the face | Cheek sebaceous pores | Whole-face pigmentation | Vascular disorders |
|---|---|---|---|---|---|---|---|---|---|
| MAE | 0.54243 | 0.40254 | 0.44798 | 0.6701 | 0.65275 | 0.55396 | 0.41607 | 0.6215 | 0.7088 |
| %(MAE < 0.5) | 56 | 70 | 63 | 45 | 46 | 53 | 68 | 49 | 50 |
| %(MAE < 1.0) | 85 | 94 | 92 | 78 | 78 | 86 | 93 | 81 | 77 |
| %(MAE < 1.5) | 97 | 100 | 99 | 93 | 94 | 97 | 99 | 94 | 88 |

Figure 4:
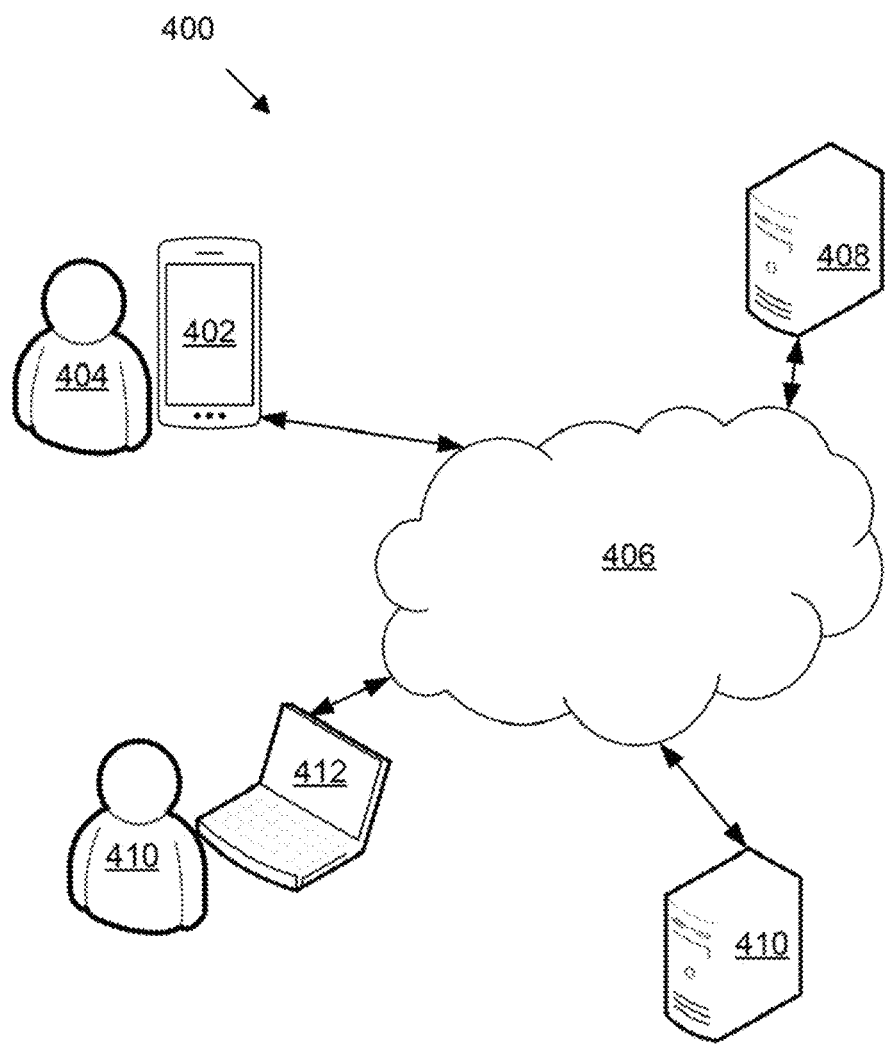
FIG. 4 is an illustration of a computer network providing an environment for various aspects according to embodiments herein.

FIG. 4 is a block diagram of an example computer network 400 in which a computing device 402 for personal use operated by a user 404 is in communication via a communications network 404 with remotely located server computing devices, namely server 406 and server 408. User 404 may be a consumer and/or a patient of a dermatologist. Also shown is a second user 410 and a second computing device 412 configured for communication via communications network 404. Second user 410 may be a dermatologist. Computing device 402 is for personal use by a user and is not available to the public such as are services from a server. Here, the public comprises registered users and/or customers, etc.

Briefly, computing device 402 is configured to perform skin diagnostics as described herein. Neural network 200 may be stored and utilized on board computing device 402 or it may be provided from server 406 such as via a cloud service, web service, etc. from image(s) received from computing device 402.

Computing device 402 is configured to communicate with server 408 for example to provide skin diagnostic information and receive product/treatment recommendations responsive to a skin diagnosis and/or other information regarding the user e.g. age, gender, etc. Computing device 402 may be configured to communicate skin diagnostic information (which may include image data) to either or both of server 406 and 408, for example, to store in a data store (not shown). Server 408 (or another servicer not shown) may provide e-commerce services to sell recommended product(s).

Computing device 402 is shown as a handheld mobile device (e.g. a smartphone or tablet). However it may be another computing device such as a laptop, desktop, workstation, etc. Skin diagnosis as described herein may be implemented on other computing device types. Computing device 402 may be configured using one or more native applications or browser-based applications, for example.

Computing device 402 may comprise a user device, for example, to acquire one or more images such as a picture of skin, particularly a face, and process the images to provide skin diagnostics. The skin diagnostics may be performed in association with a skin treatment plan where images are acquired periodically and analysed to determine skin scores for one or more skin signs. The scores may be stored (locally, remotely or both) and compared between sessions, for example to show trends, improvement, etc. Skin scores and/or skin images may be accessible to the user 404 of computing device 402 and made available (e.g. via server 406 or communicated (electronically) in another manner via communication network 404) to another user (e.g. second user 410) of computer system 400 such as a dermatologist. Second computing device 412 may also perform skin diagnostics as described. It may receive images from a remote source (e.g. computing device 402, server 406, server, 408 etc.) and/or may capture images via an optical sensor (e.g. a camera) coupled thereto or in any other manner. Neural network 200 may be stored and used from second computing device 412 or from server 406 as described.

An application may be provided to perform the skin diagnostics, suggest one or more products and monitor skin changes following one or more application of the product (which may define treatment sessions in a treatment plan) over a time period. The computer application may provide workflow such as a series of instructive graphical user interfaces (GUIs) and/or other user interfaces, which are typically interactive and receive user input, to perform any of the following activities:

skin diagnostics;
product recommendation such as for a treatment plan;
product purchase or other acquisition;
reminding, instructing and/or recording (e.g. logging) product application for respective treatment sessions;
subsequent (e.g. one or more follow up) skin diagnostics; and
present results (e.g. comparative results);

such as in accordance with a treatment plan schedule to monitor progress of a skin treatment plan. Any of these activities may generate data which may be stored remotely for example for user 410 to review, for another individual to review, for aggregation with other user's data to measure treatment plan efficacy, etc.

Comparative results (e.g. before and after results) may be presented via computing device 402 whether during and/or at the completion, etc. of a treatment plan. As noted, aspects of skin diagnostics may be performed on computing device 400 or by a remotely coupled device (e.g. a server in the cloud or another arrangement).

Figure 5:
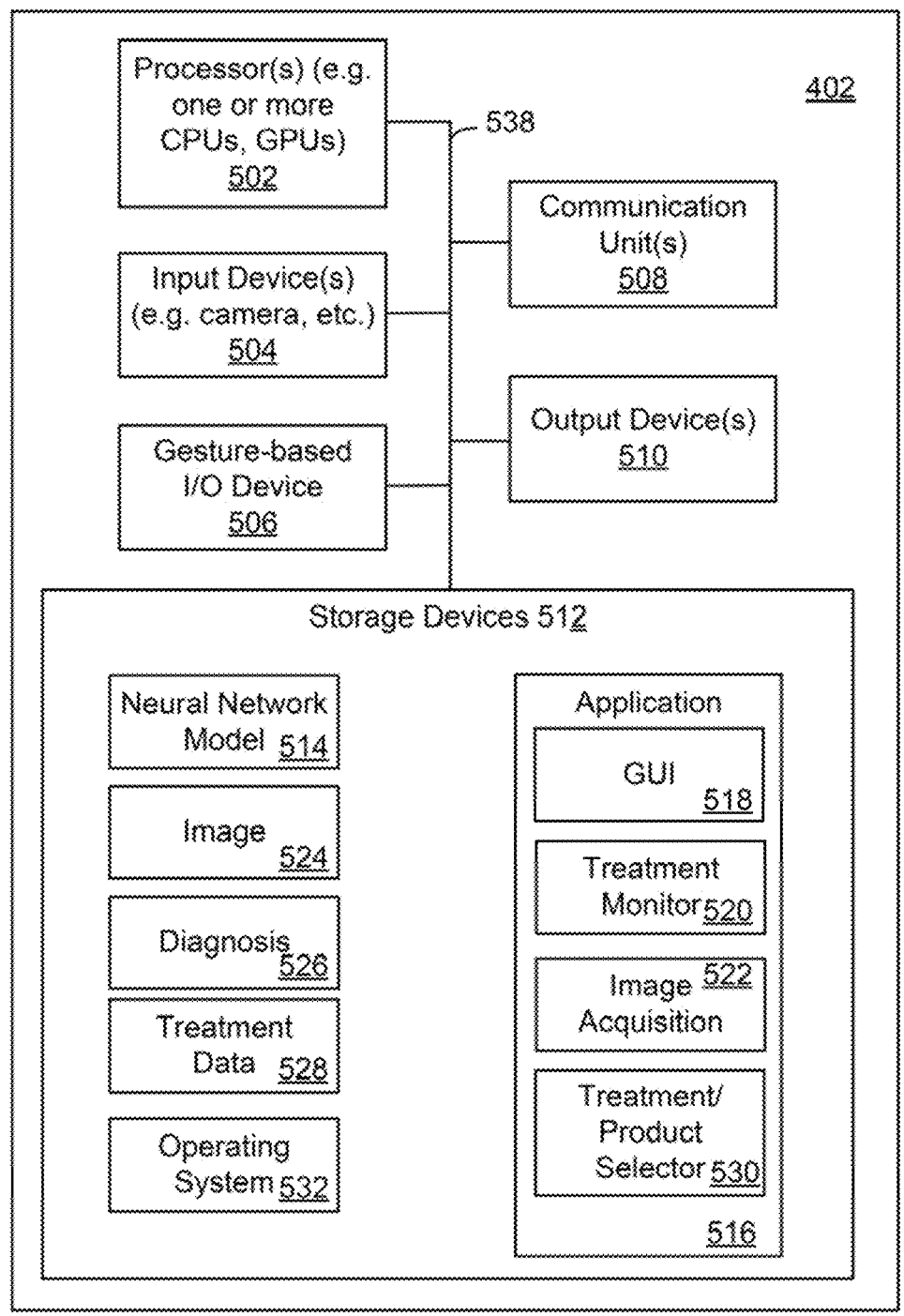
FIG. 5 is a block diagram of a computing device of the computer network of FIG. 4.

FIG. 5 is a block diagram of computing device 402, in accordance with one or more aspects of the present disclosure. Computing device 402 comprises one or more processors 502, one or more input devices 504, a gesture-based I/O device 506, one or more communication units 508 and one or more output devices 510. Computing device 402 also includes one or more storage devices 512 storing one or more modules and/or data. Modules may include deep neural network model 514, application 516 having components for a graphical user interface (GUI 518) and/or workflow for treatment monitoring (e.g. treatment monitor 520), image acquisition 522 (e.g. an interface) and treatment/product selector 530 (e.g. an interface). Data may include one or more images for processing (e.g. image 524), skin diagnosis data (e.g. respective scores, ethnicity or other user data), treatment data 528 such as logging data related to specific treatments, treatment plans with schedules such as for reminders, etc.)

Application 516 provides the functionality to acquire one or more images such as a video and process the images to determine skin diagnosis a deep neural network as provided by neural network model 514. Network model may be configured as the model shown in FIGS. 2 and 3. In another example, the network model is remotely located and computing device 402 via application 516 may communicate the image for processing and return of skin diagnosis data. Application 516 may be configured to perform the previously described activities.

Storage device(s) 512 may store additional modules such as an operating system 532 and other modules (not shown) including communication modules; graphics processing modules (e.g. for a GPU of processors 502); map module; contacts module; calendar module; photos/gallery module; photo (image/media) editor; media player and/or streaming module; social media applications; browser module; etc. Storage devices may be referenced as storage units herein.

Communication channels 538 may couple each of the components 502, 504, 506, 508, 510, 512, and any modules 514, 516 and 532 for inter-component communications, whether communicatively, physically and/or operatively. In some examples, communication channels 538 may include a system bus, a network connection, an inter-process communication data structure, or any other method for communicating data.

The one or more processors 502 may implement functionality and/or execute instructions within computing device 402. For example, processors 502 may be configured to receive instructions and/or data from storage devices 512 to execute the functionality of the modules shown in FIG. 5, among others (e.g. operating system, applications, etc.) Computing device 402 may store data/information to storage devices 512. Some of the functionality is described further herein below. It is understood that operations may not fall exactly within the modules 514, 516 and 532 of FIG. 5 such that one module may assist with the functionality of another.

Computer program code for carrying out operations may be written in any combination of one or more programming languages, e.g., an object oriented programming language such as Java, Smalltalk, C++ or the like, or a conventional procedural programming language, such as the "C" programming language or similar programming languages.

Computing device 402 may generate output for display on a screen of gesture-based I/O device 506 or in some examples, for display by a projector, monitor or other display device. It will be understood that gesture-based I/O device 506 may be configured using a variety of technologies (e.g. in relation to input capabilities: resistive touchscreen, a surface acoustic wave touchscreen, a capacitive touchscreen, a projective capacitance touchscreen, a pressure-sensitive screen, an acoustic pulse recognition touchscreen, or another presence-sensitive screen technology; and in relation to output capabilities: a liquid crystal display (LCD), light emitting diode (LED) display, organic light-emitting diode (OLED) display, dot matrix display, e-ink, or similar monochrome or color display).

In the examples described herein, gesture-based I/O device 506 includes a touchscreen device capable of receiving as input tactile interaction or gestures from a user interacting with the touchscreen. Such gestures may include tap gestures, dragging or swiping gestures, flicking gestures, pausing gestures (e.g. where a user touches a same location of the screen for at least a threshold period of time) where the user touches or points to one or more locations of gesture-based I/O device 506. Gesture-based I/O device 506 and may also include non-tap gestures. Gesture-based I/O device 506 may output or display information, such as graphical user interface, to a user. The gesture-based I/O device 506 may present various applications, functions and capabilities of the computing device 402 including, for example, application 516 to acquire images, view images, process the images and display new images, messaging applications, telephone communications, contact and calendar applications, Web browsing applications, game applications, e-book applications and financial, payment and other applications or functions among others.

Although the present disclosure illustrates and discusses a gesture-based I/O device 506 primarily in the form of a display screen device with I/O capabilities (e.g. touchscreen), other examples of gesture-based I/O devices may be utilized which may detect movement and which may not comprise a screen per se. In such a case, computing device 402 includes a display screen or is coupled to a display apparatus to present new images and GUIs of application 516. Computing device 402 may receive gesture-based input from a track pad/touch pad, one or more cameras, or another presence or gesture sensitive input device, where presence means presence aspects of a user including for example motion of all or part of the user.

One or more communication units 508 may communicate with external devices (e.g. server 406, server 408, second computing device 412) such as for the purposes as described and/or for other purposes (e.g. printing) such as via communications network 404 by transmitting and/or receiving network signals on the one or more networks. The communication units may include various antennae and/or network interface cards, chips (e.g. Global Positioning Satellite (GPS)), etc. for wireless and/or wired communications.

Input devices 504 and output devices 510 may include any of one or more buttons, switches, pointing devices, cameras, a keyboard, a microphone, one or more sensors (e.g. biometric, etc.), a speaker, a bell, one or more lights, a haptic (vibrating) device, etc. One or more of same may be coupled via a universal serial bus (USB) or other communication channel (e.g. 538). A camera (an input device 804) may be front-oriented (i.e. on a same side as) to permit a user to capture image(s) using the camera while looking at the gesture based I/O device 506 to take a "selfie".

The one or more storage devices 512 may take different forms and/or configurations, for example, as short-term memory or long-term memory. Storage devices 512 may be configured for short-term storage of information as volatile memory, which does not retain stored contents when power is removed. Volatile memory examples include random access memory (RAM), dynamic random access memory (DRAM), static random access memory (SRAM), etc. Storage devices 512, in some examples, also include one or more computer-readable storage media, for example, to store larger amounts of information than volatile memory and/or to store such information for long term, retaining information when power is removed. Non-volatile memory examples include magnetic hard discs, optical discs, floppy discs, flash memories, or forms of electrically programmable memory (EPROM) or electrically erasable and programmable (EEPROM) memory.

Though not shown, a computing device may be configured as a training environment to train neural network model 514 for example using the network as shown in FIG. 3 along with appropriate training and/or testing data.

The deep neural network may be adapted to a light architecture for a computing device that is a mobile device (e.g. a smartphone or tablet) having fewer processing resources than a "larger" device such as a laptop, desktop, workstation, server or other comparable generation computing device.

In one aspect, the deep neural network model may be configured as a depthwise separable convolution neural network comprising convolutions in which individual standard convolutions are factorized into a depthwise convolution and a pointwise convolution. The depthwise convolution is limited to applying a single filter to each input channel and the pointwise convolution is limited to combining outputs of the depthwise convolution.

It is understood that second computing device 412 may be similarly configured as computing device 402. Second computing device 412 may have GUIs such as to request and display image(s) and skin sign diagnoses from data stored at server 406 for different users, etc.

FIGS. 6A-6D are flowcharts of operations 600, 610, 620 and 630 respectively such as for computing device 402 (or 410) in accordance with an example. Operations 600 relate to a user of computing device 402 using an application such as application 516 to take a selfie comprising an image of the user's face to perform skin diagnoses for a plurality (N) of respective skin signs. At 601, the image is received at the processor such as via a camera or other manner (e.g. from a message attachment).

At 602, the image is pre-processed to define a normalized image to present to the CNN. The image may be centered and cropped to a specific size (resolution) to present like sized images to CNN as per its training. At 603, the normalized image is processed using the CNN (neural network model 514) to generate the N skin sign diagnoses. The ethnicity vector is also generated. The N skin sign diagnoses and ethnicity vector (or a single value thereof) is presented at 604 such as via a GUI which may also present the image and/or normalized image. Presenting the image may comprise segmenting the image (or normalized image) for each (or at least one) of the N skin signs, indicating which region(s) of face relates to which skin sign. An extract from the image may be made such as using a bounding box and/or mask to isolate a region for which a skin sign diagnosis was prepared for presentation in a GUI. The CNN may be configured to output segmentation related data that may comprise the bounding box and/or mask for each (or at least one) particular region. The image may be annotated such as via augmented reality or virtual reality techniques to highlight the region. By way of example, relevant pixels of a region in the image may be highlighted. A GUI may be provided showing the image (or normalized image). Input may be received such as from a pointing device or gesture to indicate or select one or more pixels of a region where a skin sign diagnosis was generated by the CNN. Pixels outside the indicated region may be blurred to highlight the pixels of the selected region using a mask and/or bounding box for the region. Rather than blurring, pixels outside the region such as within a border thereof (e.g. between 1 and X pixels) may be coloured using a highlighting colour to encircle the region, creating a halo effect. Pixels immediately adjacent the region may be darker (deeper in colour) and pixels further away (within the border) may be lighter in colour. Different sign signs may have different color borders. The skin sign diagnosis for the region may be displayed. Colour may be used to indicate a severity that is proportional to the skin sign diagnosis such a using a scaling factor. A single colour may be used for a particular skin sign diagnosis and its depth of colour (e.g. light to dark) adjusted proportional to a scale of the skin sign diagnosis. In another example, different colours may be used for each level in the scale of the skin sign diagnosis. A colour legend showing the relationship to the scale may be provided, whether the GUI shows a single color varied by depth or by using different colors. A user toggle control may be provided to turn on and off the augmented reality or virtual reality applied to the image, e.g. to turn on and off the highlighting, etc. Clinical example images (or extractions of particular affected regions) showing representative images of others illustrating each of the skin sign diagnosis (e.g. one for each severity and for each skin sign) may be presented as a comparator and such examples may be shown in a manner that respects the privacy of others. As further described below, a product and/or treatment recommendation may be presented. As further described below, before and after images (e.g. where an after image represents a subsequent image taken following one or more treatments and may have a subsequent skin sign diagnosis prepared as a comparison. While a gesture input via an image is described to select or indicate a region, a GUI may be provided which automatically selects a region such as by receiving input for a specific skin sign. For example, a GUI may present a table or other form of output to present each skin sign and/or skin sign diagnosis. Selecting a particular item from the table or other form may invoke the GUI to present the image (or normalized image) with the region(s) associated with the skin sign diagnosis highlighted. It is understood that a voice-activated GUI in addition to or rather than a gesture-activated GUI (and/or other input activate-GUI (e.g. text command)) may also be used in any of the examples herein.

Figure 6A:
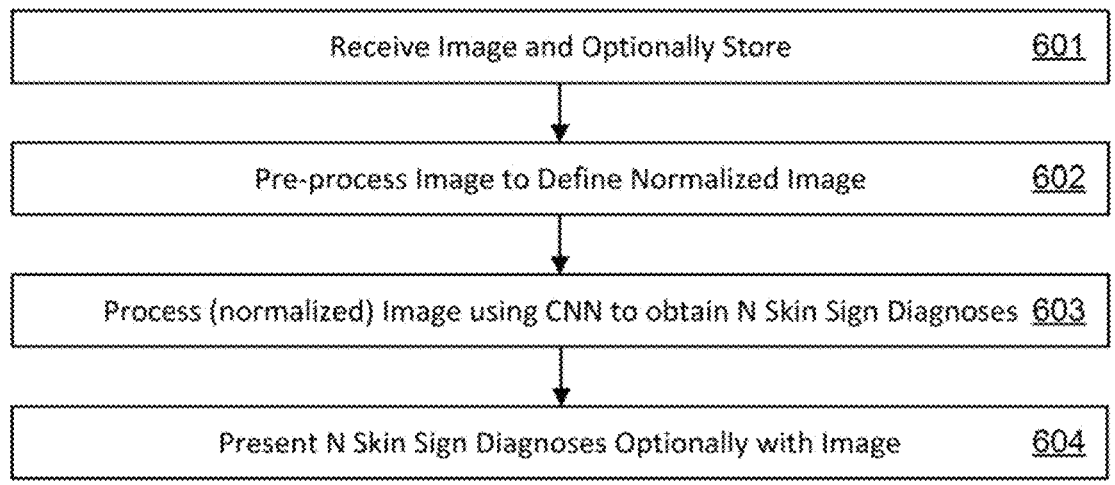
FIGS. 6A, 6B, 6C and 6D are flowcharts of operations of a computing device according to an embodiment herein.
Figure 6B:
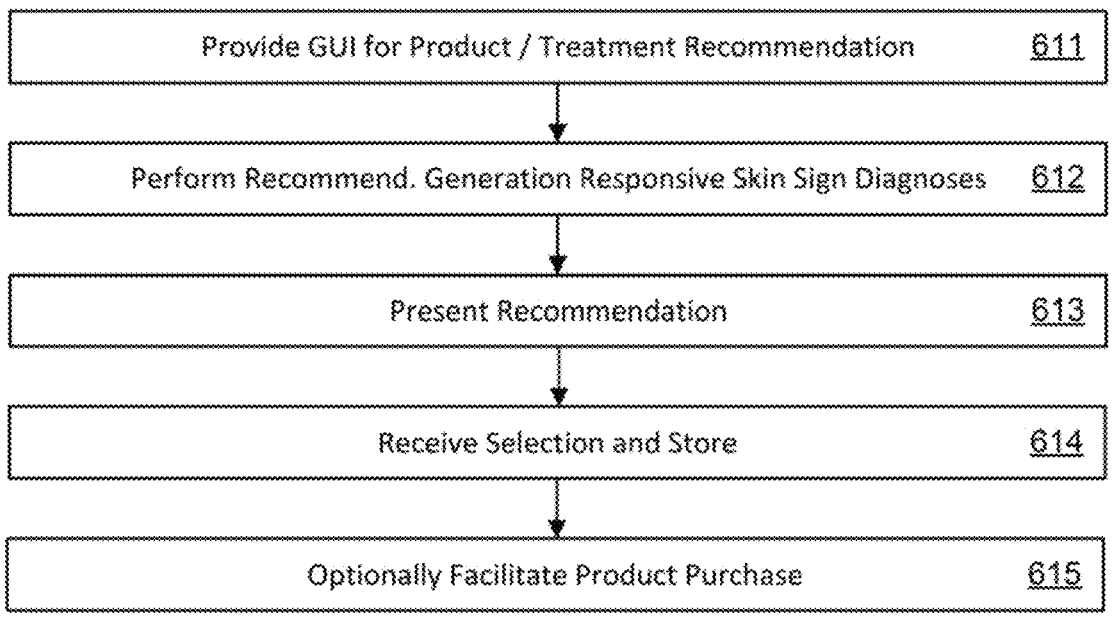

FIG. 6B shows operations 610. At 611 a GUI is presented (note that a GUI may be presented for any of the operations 600, 610, 620 and 630) to initiate a product and/or treatment recommendation. Input may be received to invoke a performance. At 612 a recommendation is received and performance may comprise communication skin diagnoses information (e.g. scores, ethnicity vector, image, user information, etc.) to a remote server such as server 408 to receive a recommendation. The recommendation may include a product or products and a regime of application to an area of skin and in association with a treatment plan having a schedule. At 613 the recommendation is presented such as via the GUI. More than one recommendation may be received and presented. At 614 a selection is made indicating acceptance of a recommendation. This may be stored (logged) and may initiate a treatment monitoring feature or function of computing device 402, for example. At 615, a product purchase may be facilitated such as via server 408, or another server.

Figure 6C:
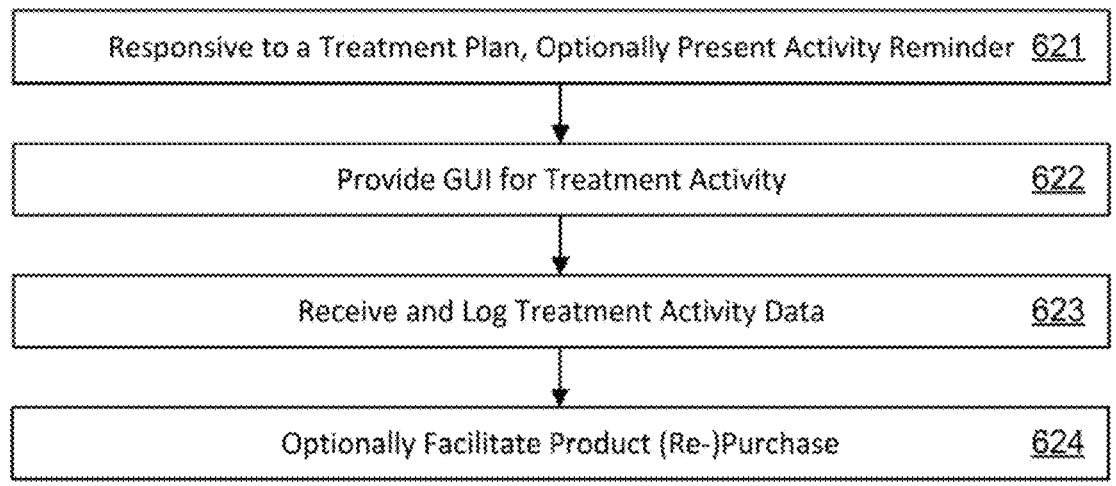
Figure 6D:
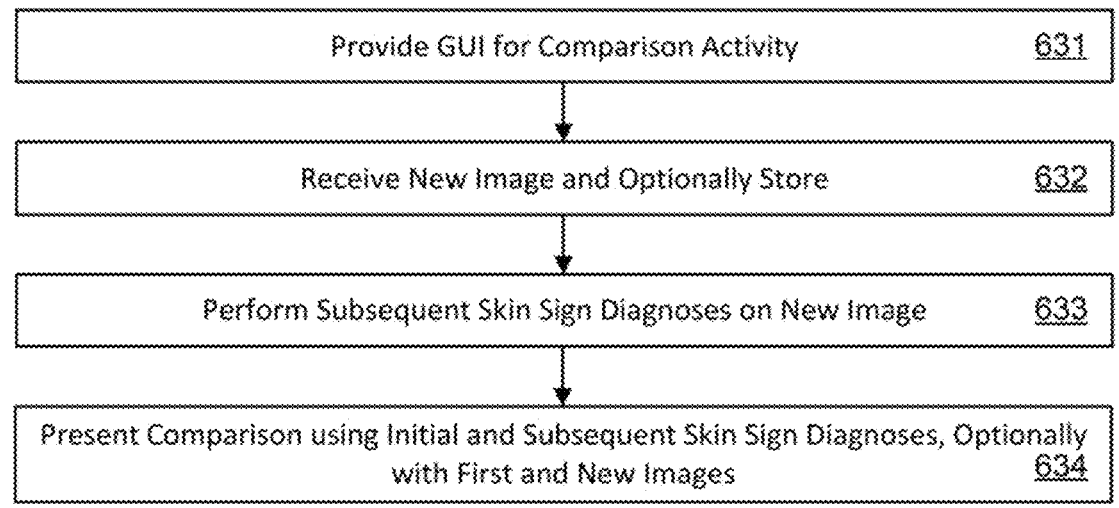

FIG. 6C shows operations 620 such as for monitoring. Monitoring may be responsive to treatment plan (e.g. described in data) received by computing device 402 or accessible to it such as via a browser. A treatment plan may have a schedule (e.g. morning and evening applications of a product, once a week application of a second product, etc. The schedule may be reminded (e.g. at 621) such as via notifications which may be native application based or via another means such as a calendar application. At 622 a GUI is provided to facilitate a treatment activity, for example to record its occurrence and/or to provide instructions to perform the activity. At 623 input is received such as a confirmation that the activity was performed. An image may be included to record the activity. The data may be logged. Monitoring may measure how closely the treatment plan is followed. At 624 product repurchase may be facilitated for example responsive to treatment monitoring it may be determined that product quantity on hand may be running out.

FIG. 6C shows operations 630 such as for performing a comparison, which may be performed as a monitoring activity. At 631, a GUI for comparison is provided to instruct a user, etc. At 632 a new image (e.g. compared to an initial image received at 601) and (optionally) stored. At 633 a subsequent skin sign diagnoses is performed using CNN on the new image (e.g. as normalized etc. similar to operations 600). At 634, a GUI present a comparison of the using the initial and subsequent skin sign diagnoses, optionally with first and new images.

Though not shown in FIGS. 6A-6D any data received or generated may be communicated for remote storage such as to server 406.

Skin sign diagnoses, and subsequent skin sign diagnoses (optionally with other monitoring) and providing data for aggregation may enable product efficacy and/or fraudulent claims study of products and treatments. The data may be gathered, analyzed and presented to dermatologists and/or other professionals and/or users. Thus the system and method herein may facilitate a distributed study model for skin treatment.

The teaching herein includes an ability to link local to global (e.g. specific conditions in a region of the face while processing the entire face) and to have an exhaustive mapping of the face targeting all the key areas—by way of example, wrinkles present in each tier of face from forehead to mouth.

A combination of local skin signs may be used to predict (classify) global appearance (e.g. apparent age, radiance, tiredness, etc.). Appearance may also be determined and compared by performing skin analysis in the presence of make-up. The skin diagnostics herein is sufficiently exhaustive in relation to the nature and position of facial signs to be able to explain the perception when other human beings are looking at the subject. The skin diagnosis of the skin signs can be used to drive a further conclusion regarding apparent age such as based on more than 95% of perception from others. In the presence of make-up, the skin diagnosis and further prediction/classification regarding a global appearance or attractiveness may be used to measure effectiveness and establish an impact of foundation, etc. to mask skin aging signs and how lines and structure of the face could be recovered.

The skin diagnosis method and techniques herein measure five clinical clusters of the face (winkles/texture, sagging, pigmentation disorders, vascular disorders, cheek pores) which facilitate data to describe all impacts of the aging process, environmental conditions (solar exposures, chronic urban pollution exposures, etc.) or lifestyles (stress, tiredness, quality of sleep, smoking, alcohol, etc). By measuring these through time, in motion or comparing them to the average of age of the consumer, the method, computing device, etc. may be configured to provide information about acceleration of aging, clear impact of environment (some of signs impact some clusters and not others . . . ) and information about:

Recommendations in term of cosmetic and/or treatment or prevention products (for example on solar exposures which kind of filters in term of geographical location, some anti-oxidants. desquamation agents, etc.)

Recommendations in term of diet, lifestyles, sports/exercise, etc., that could impact positively the damages or specificities of facial signs. It is known, for example, that facial signs can be affected by daily activities and based on that propose some strategies.

The skin diagnosis method and techniques thus described may be employed to dynamically follow consumers/patients in a highly accurate manner in all dimensions. Evaluation may be employed at different times and or different areas to evaluate day/seasonal/hormonal/rest impacts and treatment/cosmetic/health benefits. Such evaluation provides a more accurate diagnosis and enables better recommendation of solutions.

The skin diagnosis method and techniques thus described may be employed to perform evaluation on images of a user in motion such as from selfie or other videos. The method and computing device may be configured to evaluate on each frame or selected frames of a video and record facial score(s) when the face is in motion. A dynamic curve of wrinkles or sagging, etc. may be defined. The video may capture specific facial positions and transitions that induce stress in the face to assist with analysis of specific signs.

Instructions may be provided to have a user perform specific gestures, poses and the like to highlight features and impart stress to the face. In one example, the instructions (e.g. via graphical or other user interface) may request a user to perform a specific gesture to pinch the cheek for example. Such evaluation provides a more accurate diagnosis and enables better recommendation of solutions.

Other stresses may be instructed such as functional stress through body positioning, etc. where the body is upright or supine. Functional stress is very important for younger consumers to record wrinkles that could not be seen on a classical ID picture that is very neutral. Small wrinkles on eye corner could be seen when a user smiles or has specific emotions Hence, the skin diagnosis method and techniques can be enabled to receive a video when a face is in motion and then assess a number of images from it e.g. a video has frames 1, 2, ... N. Each frame can generate 20 scores for the 20 signs. The system can instruct a user to perform a gesture (face pinch) and record results. Images before and after the pinch may be analysed to conclude about skin behavior before/after stress and for example water mobility (publication DermoTrace: Flament F, Bazin R. Influences of age, ethnic group, and skin sites on a provisory skin marking, experimentally induced, in vivo. Skin Res Technol 24, 180-186 (2018).) Just two frames need be used.

The skin diagnosis method and techniques thus described may be employed to further a performance of emotional analysis by clinical feature evolution. Having a global holistic evaluation of a face may enable assessment (e.g. classification) of emotions, linking combination(s) of skin signs with specific visual signs for joy, fear, disgust, etc.

The skin diagnosis method and techniques thus described may be employed to further a performance of health care, employing the classification of the signs as showing a particular emotion such as in those unable to communicate orally or in a same language. Patients in pain can show associated emotions which can be analyzed and results used such as to administer a medicine. A combination of signs and their severities (glabellar for example) could be an essential clue in health field especially in hospitals for patients in pain who have difficulties to communicate. By reading accurately the faces one could administer medicines and specifically design treatments.

The skin diagnosis method and techniques thus described may be employed to further a performance of a characterization (e.g. classification) of the impact of environment or lifestyles. Define extrinsic aging vs intrinsic aging by comparing to database: Based on our knowledge database we know in term of quantification (% of a severity) and qualification (nature of sign and position in the face) the impact of exposure, i.e. environmental conditions (UV, Pollution . . . ) or lifestyles (stress, diet, alcohol, smoking, sports . . . ). The skin diagnostic evaluation described herein may be enhanced with information from the database to come back to consumers with a more accurate and personalized feed-back for key cosmetics topics with urban aging.

The skin diagnosis method and techniques thus described may be employed to further a performance of other medical diagnosis for other conditions. Combination(s) of skin signs could be linked to specific conditions based on research that correlate certain facial signs and specific conditions or diseases. By way of example forehead wrinkles are link with cardiac diseases.

It will be understood that the skin diagnosis method and techniques including product and or application recommendations thus described may be performed in relation to skin signs that are naturally and normally occurring and not classically associated with a disease per se (e.g. non-disease skin signs such as those related to aging and/or environmental exposures that are not indicative of a disease condition). However, the onset and/or progression of such non-disease skin signs may be responsive to respective products and respective plans of application (broadly a treatment, though not a medical treatment per se). Thus, there is provided herein a skin diagnostic device and method for non-disease skin signs such as described herein. There is provided a device and method for recommending a product for a non-disease skin signs. The device may comprise: a storage unit to store and provide a convolutional neural network (CNN) configured to classify pixels of an image to determine a plurality (N) of respective skin sign diagnoses each of a plurality (N) of respective non-disease skin signs wherein the CNN comprises a deep neural network for image classification configured to generate the N respective non-disease skin sign diagnoses and wherein the CNN is trained using non-disease skin sign data for each of the N respective non-disease skin signs; and a processing unit coupled to the storage unit configured to receive the image and process the image using the CNN to generate the N respective non-disease skin sign diagnoses. The processing unit may further be configured to generate a product recommendation for at least one of the N respective non-disease skin sign diagnoses such as by using a product recommendation component (e.g. a rules based system or other system that selects one or more products and optionally a plan of application for a respective product associated with a respective non-disease skin sign. The product recommendation component and thus a product recommendation, may be responsive to other factors such as gender, ethnicity, etc. Associated training methods and systems will be apparent to train a CNN or define a system having a CNN to generate the N respective skin sign diagnoses will also be apparent.

In addition to computing device aspects, a person of ordinary skill will understand that computer program product aspects are disclosed, where instructions are stored in a non-transient storage device (e.g. a memory, CD-ROM, DVD-ROM, disc, etc.) to configure a computing device to perform any of the method aspects stored herein.

Practical implementation may include any or all of the features described herein. These and other aspects, features and various combinations may be expressed as methods, apparatus, systems, means for performing functions, program products, and in other ways, combining the features described herein. A number of embodiments have been described. Nevertheless, it will be understood that various modifications can be made without departing from the spirit and scope of the processes and techniques described herein. In addition, other steps can be provided, or steps can be eliminated, from the described process, and other components can be added to, or removed from, the described systems. Accordingly, other embodiments are within the scope of the following claims.

Throughout the description and claims of this specification, the word "comprise" and "contain" and variations of them mean "including but not limited to" and they are not intended to (and do not) exclude other components, integers or steps. Throughout this specification, the singular encompasses the plural unless the context requires otherwise. In particular, where the indefinite article is used, the specification is to be understood as contemplating plurality as well as singularity, unless the context requires otherwise.

Features, integers characteristics, compounds, chemical moieties or groups described in conjunction with a particular aspect, embodiment or example of the invention are to be understood to be applicable to any other aspect, embodiment or example unless incompatible therewith. All of the features disclosed herein (including any accompanying claims, abstract and drawings), and/or all of the steps of any method or process so disclosed, may be combined in any combination, except combinations where at least some of such features and/or steps are mutually exclusive. The invention is not restricted to the details of any foregoing examples or embodiments. The invention extends to any novel one, or any novel combination, of the features disclosed in this specification (including any accompanying claims, abstract and drawings) or to any novel one, or any novel combination, of the steps of any method or process disclosed.

What we claim is:

1. A skin diagnostic device comprising:
a memory configured to store and provide a convolutional neural network (CNN) configured to classify pixels of an image to determine a plurality (N) of respective skin sign diagnoses for each of a plurality (N) of respective skin signs wherein the CNN comprises a deep neural network for image classification configured to generate the N respective skin sign diagnoses and wherein the CNN is trained using skin sign data for each of the N respective skin signs; and
at least one processor coupled to the memory and configured to receive the image and process the image using the CNN to generate the N respective skin sign diagnoses,
wherein the CNN comprises:
an encoder phase for image classification and configured to encode features to a final encoder phase feature net; and
a decoder phase configured to receive the final encoder phase feature net for decoding by a plurality (N) of respective parallel skin sign branches to generate each of the N respective skin sign diagnoses.

2. The skin diagnostic device according to claim 1, wherein the decoder phase includes a global pooling operation to process the final encoder phase feature net to provide to each of the N respective parallel skin sign branches.

3. The skin diagnostic device according to claim 1, wherein the CNN is further configured to classify the pixels to determine an ethnicity vector and the CNN is trained using skin sign data for each of the N respective skin signs and a plurality of ethnicities.

4. The skin diagnostics device according to claim 3, wherein the decoder phase comprises a further parallel branch for ethnicity to generate the ethnicity vector.

5. The skin diagnostic device according to claim 1, wherein each branch of the N respective parallel skin sign branches comprises in succession: a first fully connected layer followed, a first activation layer, a second fully connected layer, a second activation layer and a final activation layer to output a final value comprising one of the N respective skin sign diagnoses and the ethnicity vector.

6. The skin diagnostic device according to claim 5, wherein the final activation layer is defined in accordance with a function of equation (1) for an input score x received from the second activation layer:

$$LeakyClamp(x) = \begin{cases} x & \text{if } x \in [a, b] \\ \alpha(x-a)+a & \text{if } x < a \\ \alpha(x-b)+b & \text{if } x > b \end{cases} \quad (1)$$

where $\alpha$ is a slope, a is a lower bound and b is an upper bound of a respective score range for each the N respective skin sign diagnoses.

7. The skin diagnostic device according to claim 4:
wherein the CNN is trained using multiple samples in the form $(x_i, y_i)$, with $x_i$ being the i-th training image and $y_i$ being a corresponding vector of ground truth skin sign diagnoses; and
wherein the CNN is trained to minimize a loss function for each respective branch of the N parallel skin sign branches and the further parallel branch for ethnicity.

8. The skin diagnostic device according to claim 7, wherein the CNN is further trained to minimize a loss function L, comprising a L2 loss function for each of the N respective skin sign branches in a weighted combination with a standard cross-entropy classification loss $L_{ethnicity}$ for the further parallel branch for ethnicity, according to equation (3):

$$L = L2 + \lambda L_{ethnicity} \quad (3)$$

where $\lambda$ controls a balance between a score regression and ethnicity classification losses.

9. The skin diagnostic device according to claim 1, wherein the memory stores a face and landmark detector to pre-process the image and wherein the at least one processor is configured to generate a normalized image from the image using the face and landmark detector and use the normalized image when using the CNN.

10. The skin diagnostic device according to claim 1, wherein the CNN comprises a pre-trained network for image classification which is adapted to generate the N respective skin sign diagnoses such that:
the fully connected layers of the pre-trained network are removed; and
N respective groups of layers are defined to decode a same feature net for each of the N respective skin sign diagnoses in parallel.

11. The skin diagnostic device according to claim 1, configured as one of:
 a computing device for personal use comprising a mobile device; and
 a server providing skin diagnostic services via a communications network.

12. The skin diagnostic device according to claim 1, wherein the memory stores code which when executed by the at least one processor provides a treatment product selector responsive to at least some of the N skin sign diagnoses to obtain a recommendation for one or both of a product and a plan for treatment.

13. The skin diagnostic device according to claim 12, wherein the memory stores code which when executed by the at least one processor provides a product purchase interface to purchase one or more products.

14. The skin diagnostic device according to claim 1, wherein the memory stores code which when executed by the at least one processor provides a treatment monitor to monitor treatment for at least one skin sign.

15. The skin diagnostic device according to claim 14, wherein the at least one processor is configured to at least one of remind, instruct and/or record treatment activities associated with a product application for respective treatment sessions.

16. The skin diagnostic device according to claim 1, wherein the at least one processor is configured to process a second image using the CNN to generate a subsequent skin diagnoses received following a treatment session.

17. The skin diagnostic device according to claim 16, wherein the memory stores code which when executed by the at least one processor provide a presentation of comparative results using the subsequent skin diagnoses.

18. A method implemented by a skin diagnostic device comprising:
 storing and providing, by a memory of the skin diagnostic device, a convolutional neural network (CNN) configured to classify pixels of an image to determine a plurality (N) of respective skin sign diagnoses for each of a plurality (N) of respective skin signs wherein the CNN comprises a deep neural network for image classification configured to generate the N respective skin sign diagnoses and wherein the CNN is trained using skin sign data for each of the N respective skin signs; and
 performing by at least one processor of the skin diagnostic device that is coupled to the memory:
 receiving the image; and
 processing the image using the CNN to generate the N respective skin sign diagnoses,
 wherein the CNN comprises:
 an encoder phase defined for image classification and configured to encode features to a final encoder phase feature net; and
 a decoder phase configured to receive the final encoder phase feature net for decoding by a plurality (N) of respective parallel skin sign branches to generate each of the N respective skin sign diagnoses.

19. The method of claim 18, wherein the at least one processor of the skin diagnostic device provides any one or more of:
 a treatment product interface responsive to at least some of the N skin sign diagnoses to obtain a recommendation for at least one or both of a product and a plan for treatment;
 a product purchase interface to purchase one or more products;
 a treatment monitor to monitor treatment for at least one skin sign;
 a comparative results interface to present comparative results using a second skin diagnoses obtained in accordance with the method when processing a second image.

20. A method implemented by at least one processor of a computer comprising:
 training a convolutional neural network (CNN) configured to classify pixels of an image to determine a plurality (N) of respective skin sign diagnoses for each of a plurality (N) of respective skin signs wherein the CNN comprises a deep neural network for image classification configured to generate the N respective skin sign diagnoses and wherein the training is performed using skin sign data for each of the N respective skin signs,
 wherein the CNN comprises:
 an encoder phase defined for image classification and configured to encode features to a final encoder phase feature net; and
 a decoder phase configured to receive the final encoder phase feature net for decoding by a plurality (N) of respective parallel skin sign branches to generate each of the N respective skin sign diagnoses.

\* \* \* \* \*